(12) United States Patent
Brown et al.

(10) Patent No.: US 10,217,623 B2
(45) Date of Patent: Feb. 26, 2019

(54) SECONDARY ELECTROSPRAY IONIZATION AT REDUCED PRESSURE

(71) Applicant: Micromass UK Limited, Wilmslow (GB)

(72) Inventors: Jeffery Mark Brown, Hyde (GB); David Gordon, Manchester (GB); Daniel James Kenny, Knutsford (GB); Paul Murray, Manchester (GB)

(73) Assignee: MICROMASS UK LIMITED, Wilmslow (GB)

( * ) Notice: Subject to any disclaimer, the term of this patent is extended or adjusted under 35 U.S.C. 154(b) by 31 days.

(21) Appl. No.: 15/317,731

(22) PCT Filed: Jun. 12, 2015

(86) PCT No.: PCT/GB2015/000176
§ 371 (c)(1),
(2) Date: Dec. 9, 2016

(87) PCT Pub. No.: WO2015/189548
PCT Pub. Date: Dec. 17, 2015

(65) Prior Publication Data
US 2017/0125232 A1  May 4, 2017

(30) Foreign Application Priority Data

Jun. 12, 2014 (EP) .................................... 14172122
Jun. 12, 2014 (GB) .................................... 1410472.3

(51) Int. Cl.
*H01J 49/16* (2006.01)
*H01J 49/14* (2006.01)
(Continued)

(52) U.S. Cl.
CPC .......... *H01J 49/165* (2013.01); *G01N 27/622* (2013.01); *H01J 49/0031* (2013.01); *H01J 49/145* (2013.01); *H01J 49/24* (2013.01)

(58) Field of Classification Search
None
See application file for complete search history.

(56) References Cited

U.S. PATENT DOCUMENTS 2,930,917 A  2/1958 Nief
5,828,062 A  10/1998 Jarrell et al.
(Continued)

FOREIGN PATENT DOCUMENTS

DE  44 14 403  4/1994
DE  4414403 A1 * 10/1994 ............ H01J 49/145

*Primary Examiner* — Andrew Smyth
(74) *Attorney, Agent, or Firm* — Womble Bond Dickinson (US) LLP; Deborah M. Vernon; Heath T. Misley (57) ABSTRACT

A method of mass spectrometry or ion mobility spectrometry is disclosed comprising: providing gas phase analyte in a vacuum housing; electrospraying a reagent solution outside of the vacuum housing so as to form charged droplets of reagent solution and/or reagent ions; conveying the charged droplets and/or reagent ions into the vacuum housing and reacting them with the analyte so as to form analyte ions; and analyzing the analyte ions with a mass analyzer and/or ion mobility analyzer. Reacting the droplets of reagent solution and/or reagent ions with the analyte in sub-atmospheric pressures improved the reaction conditions.

13 Claims, 7 Drawing Sheets

(51) Int. Cl.
   *G01N 27/62*   (2006.01)
   *H01J 49/00*   (2006.01)
   *H01J 49/24*   (2006.01)

(56) References Cited

U.S. PATENT DOCUMENTS

| | | | |
|---|---|---|---|
| 8,063,362 B1 | 11/2011 | Dressler et al. | |
| 8,173,960 B2 * | 5/2012 | Tang | H01J 49/0431 250/281 |
| 8,410,433 B2 | 4/2013 | Wuest et al. | |
| 8,525,105 B2 | 9/2013 | Whitehouse et al. | |
| 8,704,170 B2 * | 4/2014 | Kumashiro | H01J 49/066 250/288 |
| 8,927,295 B2 | 1/2015 | Hassell et al. | |
| 2008/0179511 A1 | 7/2008 | Chen et al. | |
| 2009/0095899 A1 * | 4/2009 | Whitehouse | H01J 49/0027 250/282 |
| 2009/0152458 A1 | 6/2009 | Vilkov et al. | |

* cited by examiner

SECONDARY ELECTROSPRAY IONIZATION AT REDUCED PRESSURE

CROSS-REFERENCE TO RELATED APPLICATIONS

This application represents the U.S. National Phase of International Application number PCT/GB2015/000176 entitled "Secondary Electrospray Ionization at Reduced Pressure" filed 12 Jun. 2015, which claims priority from and the benefit of United Kingdom patent application No. 1410472.3 filed on 12 Jun. 2014 and European patent application No. 14172122.5 filed on 12 Jun. 2014. The entire contents of these applications are incorporated herein by reference.

BACKGROUND TO THE PRESENT INVENTION

The present invention relates to the field of mass spectrometry and ion mobility spectrometry.

It is well known that if analytes carried in vapour, droplets or gases are allowed to interact with an electrospray ionisation (ESI) cloud at atmospheric pressure, they become ionised. The approach of mixing a stream of gas containing species to be analysed with a flow of solvent droplets emitted from an ESI source results in the production of analyte ions, which are then transferred to the sampling orifice of a mass spectrometer or ion mobility separator. This technique is known as secondary electrospray ionisation and is performed at ambient pressures prior to the analyte entering the instrument through the sampling orifice.

The sensitivity of such secondary electrospray ionisation devices is dependent on the critical alignment of the electrospray charged droplet stream and the impinging beam of analyte, be it a gas flow carrying the analyte or a plume of ejected material such as in a LAESI technique. Further, it is then critical that the resulting charged droplet stream containing the analyte is aligned with the sampling orifice of the analyser.

It is desired to provide an improved method of mass spectrometry or ion mobility spectrometry, and an improved spectrometer for performing such a method.

SUMMARY OF THE PRESENT INVENTION

From a first aspect, the present invention provides a method of mass spectrometry or ion mobility spectrometry comprising:

providing gas phase analyte in a vacuum housing;

electrospraying a reagent solution outside of the vacuum housing so as to form charged droplets of reagent solution and/or reagent ions;

conveying the charged droplets and/or reagent ions into the vacuum housing and reacting them with the analyte so as to form analyte ions; and analysing the analyte ions with a mass analyser and/or ion mobility analyser.

The present invention ionises the analyte within the vacuum housing (i.e. at sub-atmospheric pressure). This is advantageous over conventional approaches that ionise the analyte at atmospheric pressure, because the coulombic interaction between the analyte and the reagent ions is hindered less by collisions with the ambient gas molecules at the lower pressure regimes of the present invention. Furthermore, atmospheric impurities will be at reduced levels at the lower pressure of the present invention. In addition, at low pressure, carryover of analytes as well of speed of analysis are substantially improved.

The present invention provides an alternative soft ionisation method.

The electrospraying may be performed in a region substantially at atmospheric pressure and the analyte may be reacted with said charged droplets and/or reagent ions in a region of the vacuum housing that is below atmospheric pressure.

The charged droplets and/or reagent ions may pass into the vacuum housing through an atmospheric pressure sampling orifice.

The charged droplets may enter the vacuum housing and then desolvate to form reagent ions that react with the analyte to form said analyte ions.

The analyte may be conveyed into the vacuum housing entrained in a gas.

Said step of providing analyte in the vacuum housing may comprise providing said analyte in the form of analyte molecules. Less desirably, the analyte may be provided in the form of analyte ions, for reaction with the charged droplets and/or reagent ions to form different analyte ions.

The method may comprise urging the analyte ions into the mass analyser and/or ion mobility analyser using a pressure gradient and/or electric field.

The method may comprise drawing the analyte into the vacuum housing using a pressure difference maintained between the inside and outside of the vacuum housing.

The method may comprise ionising the analyte within the vacuum housing by a further ionisation means in addition to reacting the analyte with said charged droplets and/or reagent ions.

The further means may be a glow discharge device.

The method may comprise heating a sample comprising said analyte so as to provide the gas phase analyte.

The analyte may be conveyed into the vacuum housing through a heated capillary.

The analyte may be provided in the gaseous phase by one of the means selected from the group consisting of: entraining the analyte in a carrier gas that is directed into the vacuum housing; or direct laser desorption, ablation or thermal desorption of the analyte within the reduced pressure region.

It is contemplated that the analyte may be ionised by charged droplets and/or reagent ions from sources other than an electrospray device.

Accordingly, from a second aspect the present invention provides a method of mass spectrometry or ion mobility spectrometry comprising:

providing an analyte in a vacuum region;

reacting the analyte with charged droplets of reagent solution and/or reagent ions in the vacuum region so as to form analyte ions; and analysing the analyte ions with a mass analyser and/or ion mobility analyser.

The analyte that is provided in the vacuum region may be a gas phase analyte.

The vacuum region may be a vacuum inside a vacuum housing.

The charged droplets of reagent solution and/or reagent ions may be generated by electrospraying a reagent solution.

The charged droplets and/or reagent ions may be generated outside of the vacuum region and then conveyed into the vacuum region and reacted with the analyte so as to form the analyte ions.

Means other than an electrospray source are contemplated for providing the charged droplets and/or reagent ions including, for example, sonic spray, atmospheric pressure chemical ionisation (APCI), glow discharge, corona discharge, laser-spray, AP-MALDI, ASAP, APPI, etc.

The method may comprise electrospraying a solution comprising the analyte, optionally in a region outside of the vacuum housing and conveying the electrosprayed analyte into the vacuum housing.

The solution that is electrosprayed may further comprise a reagent solution that is electrosprayed so as to form said droplets of reagent solution and/or reagent ions.

The electrosprayed analyte that is not ionised by said electrospraying may be ionised in the vacuum region by reacting with the charged droplets of reagent solution and/or reagent ions so as to form analyte ions.

The electrospraying may ionise polar analyte molecules so as to form analyte ions.

An ionisation source may be provided in said vacuum region for ionising at least some of said analyte within the vacuum region, optionally wherein said ionisation source ionises non-polar analyte molecules.

The ionisation source may be a glow discharge device. Other ionisation sources are also contemplated.

The method may comprise any one or combination of any two or more of the optional features described above in relation to the first aspect of the present invention.

For example, where electrospraying is used, it may be performed outside of the vacuum housing in a region substantially at atmospheric pressure.

The analyte vacuum region is maintained below atmospheric pressure.

The method may comprise urging the analyte ions into the mass analyser and/or ion mobility analyser using a pressure gradient and/or electric field.

The method may comprise drawing the analyte into the vacuum region using a pressure difference maintained between the inside and outside of the vacuum region.

The method may comprise heating a sample comprising said analyte so as to provide gas phase analyte.

The analyte may be conveyed into the vacuum region through a heated capillary.

The analyte may be provided in a gaseous phase by one of the means selected from the group consisting of: entraining the analyte in a carrier gas that is directed into the vacuum region; or direct laser desorption, ablation or thermal desorption of the analyte within the vacuum region.

The first aspect of the present invention also provides a mass spectrometer or ion mobility spectrometer comprising:
a vacuum housing;
means for providing gas phase analyte in or to the vacuum housing;
an electrosprayer arranged outside of the vacuum housing;
means for supplying a reagent solution to the electrosprayer for electrospraying charged droplets of reagent solution and/or reagent ions from the electrosprayer;
means for conveying the charged droplets and/or reagent ions into the vacuum housing for reacting them with the analyte so as to form analyte ions; and
a mass analyser and/or ion mobility analyser for analysing the analyte ions.

The spectrometer may be arranged and configured to perform any one of the methods described in relation to the first aspect of the present invention.

The second aspect of the present invention also provides a mass spectrometer or ion mobility spectrometer comprising:
a vacuum housing;
means for providing analyte in or to the vacuum housing;
a reagent source for supplying charged droplets of reagent solution and/or reagent ions in or to the vacuum housing for reacting with analyte in the vacuum housing to form analyte ions; and
a mass analyser and/or ion mobility analyser for analysing the analyte ions.

The spectrometer may be arranged and configured to perform any one of the methods described in relation to the second aspect of the present invention.

From another aspect, the present invention provides a method of mass spectrometry or ion mobility spectrometry comprising: providing gas phase analyte in a vacuum housing; ionising said analyte in the vacuum housing; and analysing the analyte ions with a mass analyser and/or ion mobility analyser.

From another aspect, the present invention provides a mass spectrometer or ion mobility spectrometer comprising: a vacuum housing; means for providing gas phase analyte in the vacuum housing; an ioniser within the vacuum housing for ionising said analyte in the vacuum housing; and a mass analyser and/or ion mobility analyser for analysing the analyte ions.

The spectrometer may comprise:
(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD")

fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise an electrostatic ion trap or mass analyser that employs inductive detection and time domain signal processing that converts time domain signals to mass to charge ratio domain signals or spectra. Said signal processing may include, but is not limited to, Fourier Transform, probabilistic analysis, filter diagonalisation, forward fitting or least squares fitting.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

The analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene reagent ions.

The present invention may introduce a sample gas containing an analyte species into a vacuum housing of a spectrometer at a location downstream of an atmospheric pressure sampling orifice. The sample gas may be introduced into the reduced pressure region of the vacuum housing via a capillary, whilst charged droplets from an electrospray of solvent may enter the volume via the sampling orifice. The two fluids may interact within the rarefied volume, and the electrosprayed droplets may desolvate to form ions. Charge transfers from the ions to the analyte molecules within the sample gas then occurs so as to form analyte ions. The analyte ions may then continue into the mass analyser.

BRIEF DESCRIPTION OF THE DRAWINGS

Various embodiments of the present invention will now be described, by way of example only, and with reference to the accompanying drawings in which.

DETAILED DESCRIPTION OF EMBODIMENTS

Figure 1:
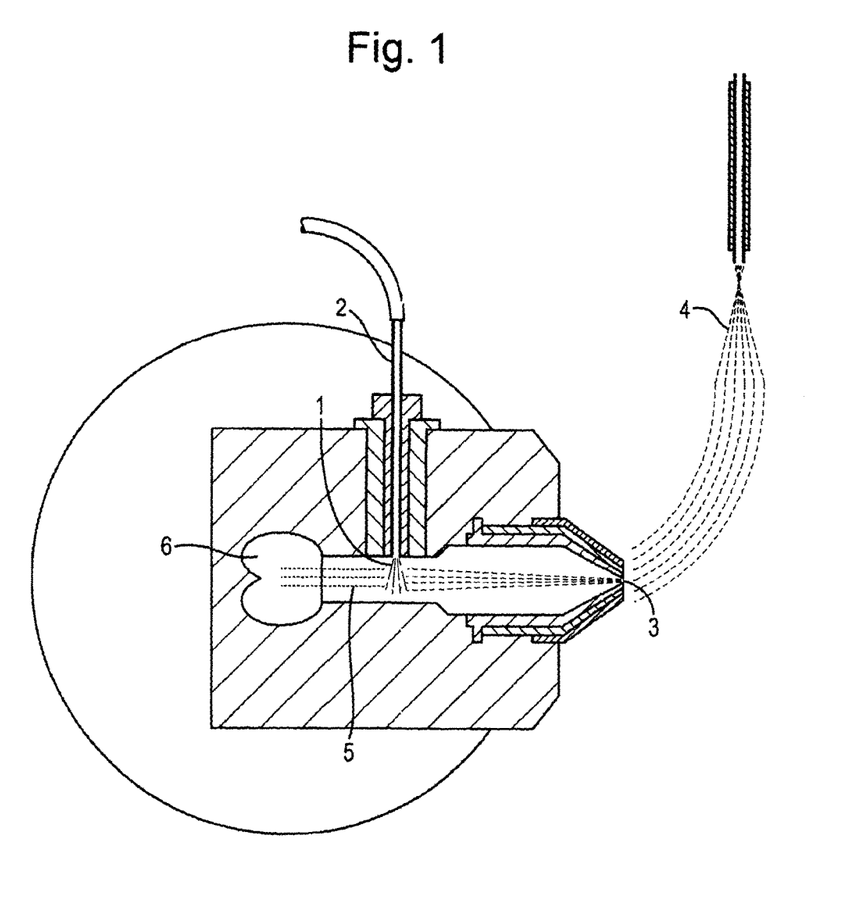
FIG. 1 shows a schematic of a spectrometer according to an embodiment of the present invention.

FIG. 1 shows a schematic of an embodiment of a mass spectrometer according to the present invention. The spectrometer comprises an atmospheric pressure Electrospray Ionisation ion (ESI) source and a mass analyser 6 arranged in a vacuum housing. An atmospheric pressure sampling orifice 3 is provided at the entrance to that vacuum housing that separates the atmospheric pressure region, in which the ESI ion source is located, from the vacuum region in the housing. An analyte supply capillary 2 is provided for supplying analyte into the vacuum housing.

During operation, sample gas carrying the analyte 1 is delivered via the capillary 2 into a volume that is located behind the atmospheric sampling orifice 3. Simultaneously, charged solvent droplets 4 are generated at atmospheric pressure by the ESI source and are drawn through the sampling orifice 3. The droplets desolvate within the reduced pressure region inside the vacuum housing to form ions. These ions interact with the analyte 1 in the sample gas flow, resulting in charge transfer to the analyte and the creation of analyte ions 5. These analyte ions 5 are then transferred to the entrance of the analyser 6 by a combination of an electric field and a pressure gradient.

The gas containing the analyte species is introduced into the instrument downstream of the atmospheric pressure sampling orifice 3 and the analyte is then ionised by the desolvated ESI ions in this low pressure region. This is advantageous over atmospheric pressure approaches, as the coulombic interaction between the analyte and the solvent ions is not hindered as much because there are fewer collisions with background gas molecules at such lower pressures. Furthermore, atmospheric impurities are at reduced levels in the low pressure region. In addition, at lower pressure, carryover of analytes and speed of analysis are substantially improved over atmospheric pressure conditions.

FIGS. 2(a) to 2(d) show mass spectra obtained by analysing Heptacosa (Perfluorotributylamine) using the embodiment of FIG. 1, but under different sampling conditions.

Figure 2A:
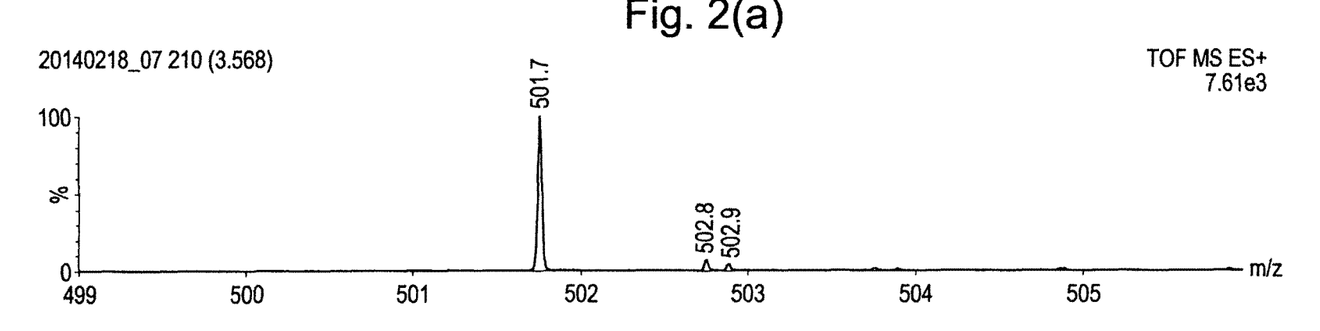
FIGS. 2(a) to 2(d) show mass spectra in a first range of mass to charge ratios that were obtained by analysing Heptacosa using the spectrometer of FIG. 1 under different sampling conditions.

The data obtained in FIG. 2(a) was obtained by passing gas through a sealed vial containing the Heptacosa and then feeding the nitrogen gas through the capillary 2 at a flow rate of 80 mL/min. A solvent consisting of 50:50 MeOH:H$_2$O was sprayed from the ESI source at a flow rate of 5 µL/min. The electrospray capillary voltage was set to 3 kV. Under these conditions, analyte ions emanating from the Heptacosa present in the carrier gas are formed by interaction with the charged solvent droplets from the ESI source. These analyte ions can be observed as peaks in the spectrum of FIG. 2(a), particularly at a mass to charge ratio of 501.7.

Figure 2B:
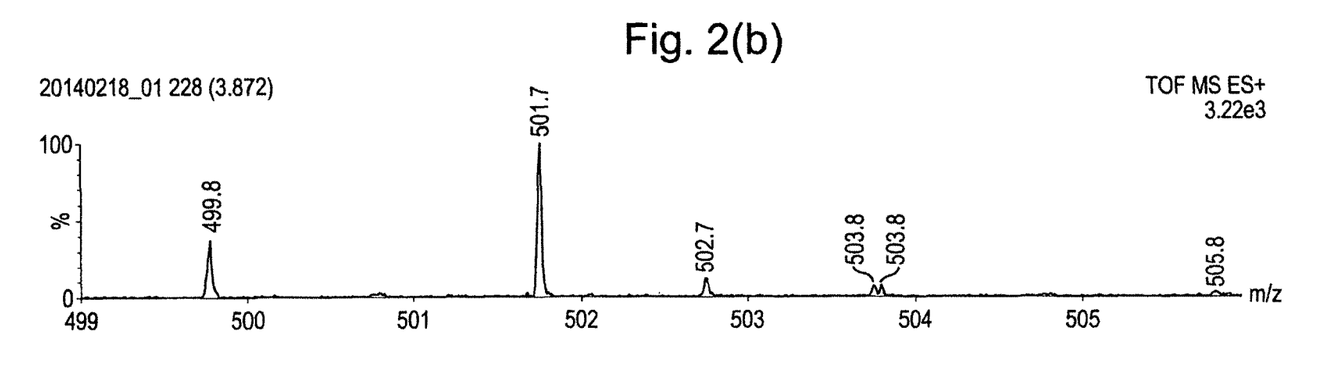

The data obtained in FIG. 2(b) was obtained by passing nitrogen gas through a sealed vial containing the Heptacosa and then feeding the nitrogen gas through the capillary 2 at a flow rate of 80 mL/min. A glow discharge was formed within the region behind the sampling orifice 3 by applying 1 kV DC to the capillary 2. The ESI source was switched off by reducing the voltage on the electrospray capillary to 0 V and stopping the solvent flow. The presence of the peaks in FIG. 2(b) confirmed that the ions observed originated from the gas flow fed through the capillary 2 and were not entering the instrument from ambient sampling of the ESI source.

Figure 2C:
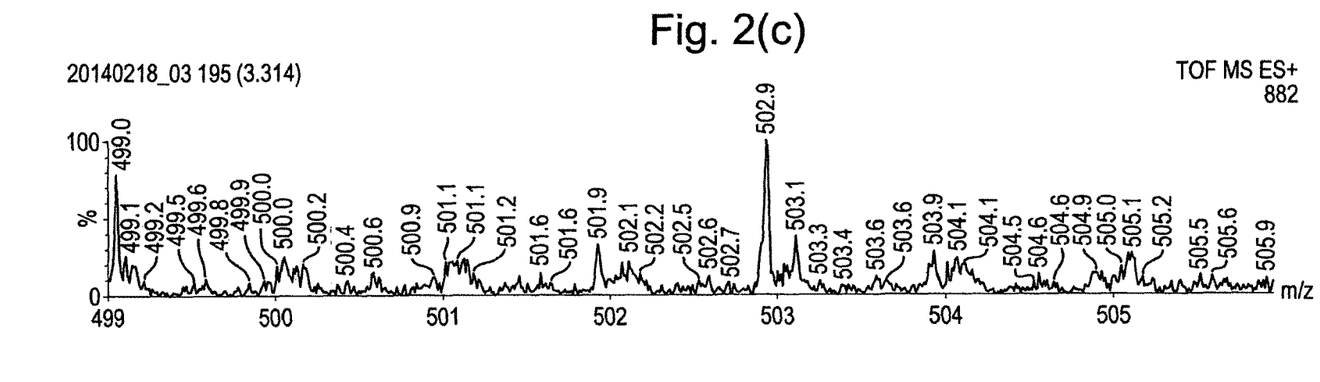

The data obtained in FIG. 2(c) was obtained by stopping the flow of carrier gas through the capillary 2, whilst spraying the 50:50 MeOH:H$_2$O solvent mixture through the ESI source at a rate of 5 µL/min with a capillary voltage of 3 kV. The absence of analyte ions in the spectra of FIG. 2(c) provides further confirmation that the analyte is not introduced into the instrument from the ESI source.

Figure 2D:
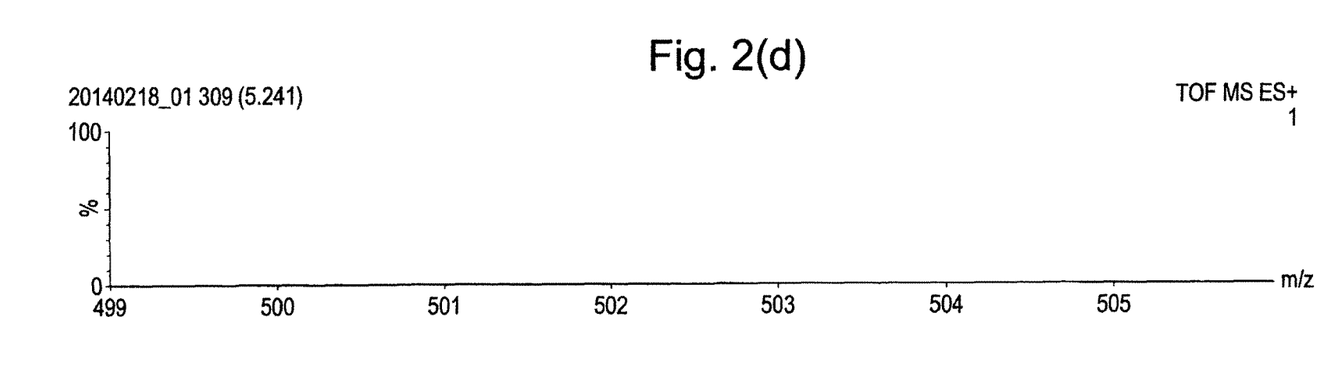

The data obtained in FIG. 2(d) was obtained by passing nitrogen gas through a sealed vial containing the Heptacosa and then feeding the nitrogen gas through the capillary 2 at a flow rate of 80 mL/min. The ESI source flow was switched off and no voltage was applied to the electrospray capillary. Also, no voltage was applied to the carrier gas capillary 2 and so no glow discharge was formed. The spectrum of FIG. 2(d) confirmed that in the absence of the described ionisation mechanisms, no analyte ions were observed.

Figure 3A:
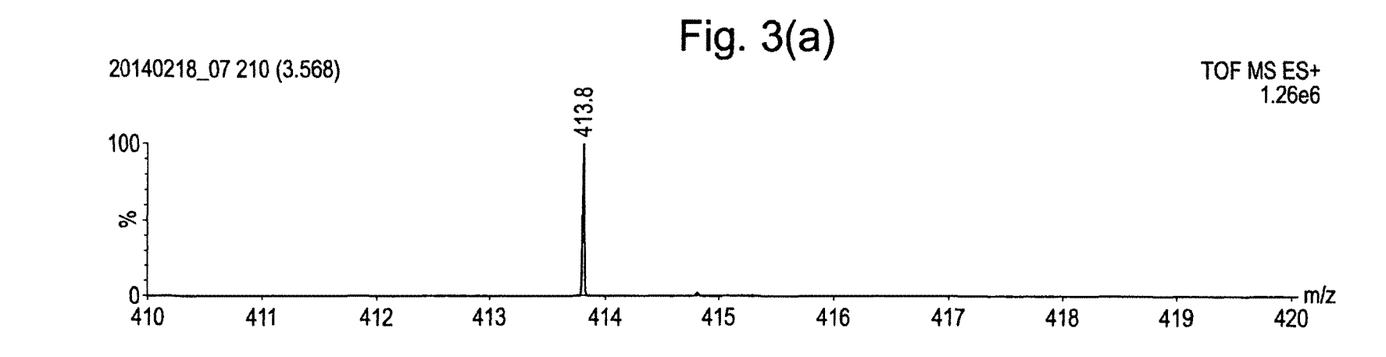
FIGS. 3(a) to 3(d) show mass spectra in a second range of mass to charge ratios that were obtained by analysing Heptacosa using the spectrometer of FIG. 1 under different sampling conditions.
Figure 3B:
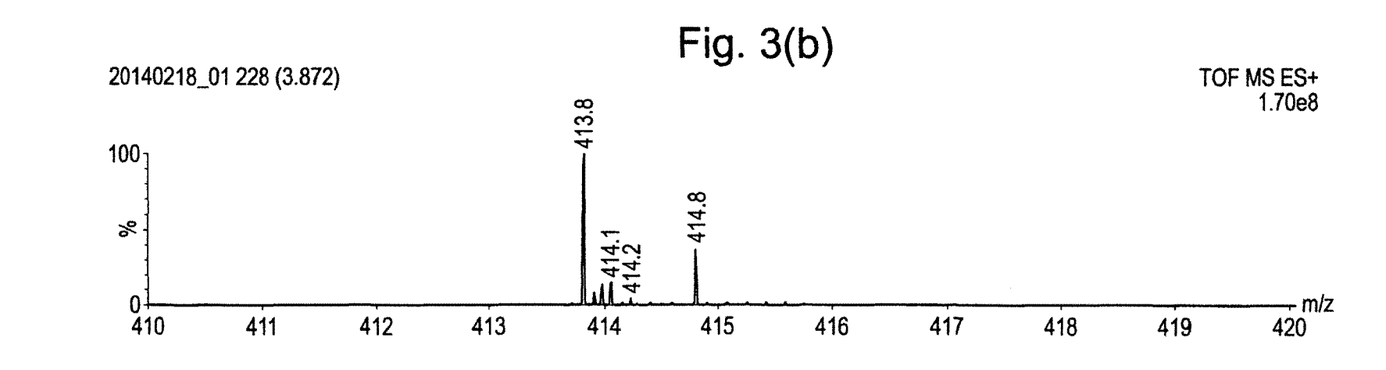
Figure 3C:
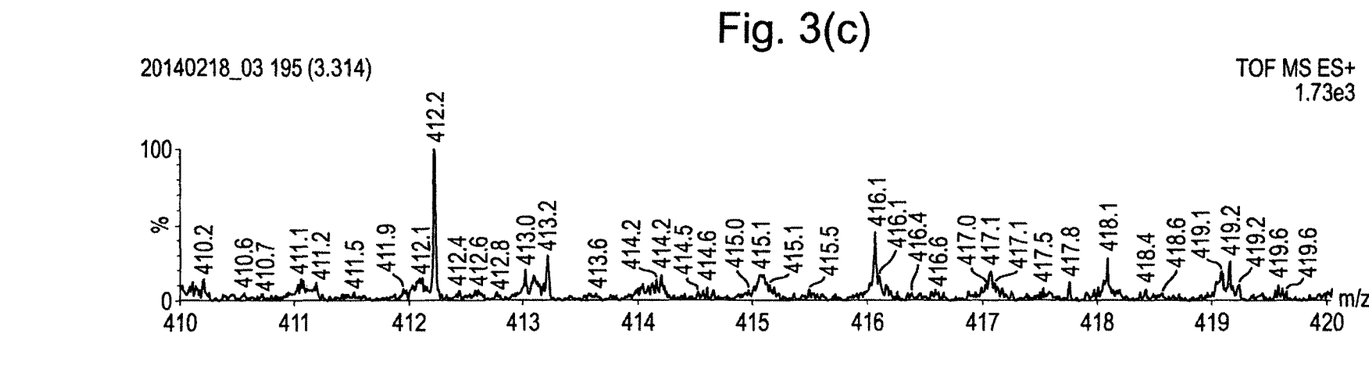
Figure 3D:
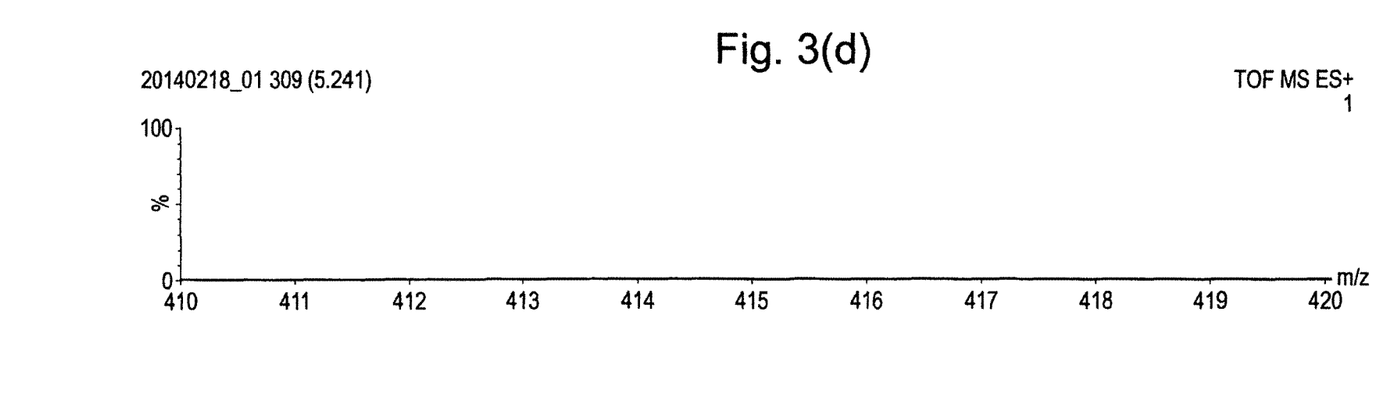

FIGS. 3(a) to 3(d) show spectra obtained under the same conditions as those of FIGS. 2(a) to 2(d), respectively, except that FIGS. 3(a) to 3(d) show the spectra for a different range of mass to charge ratios. FIGS. 3(a) and 3(b) show that a peak associated with Heptacosa is observed at a mass to charge ratio of 413.8. This peak is not observed in FIGS. 3(c) and 3(d), confirming that the analyte is ionised in the vacuum housing.

Figure 4A:
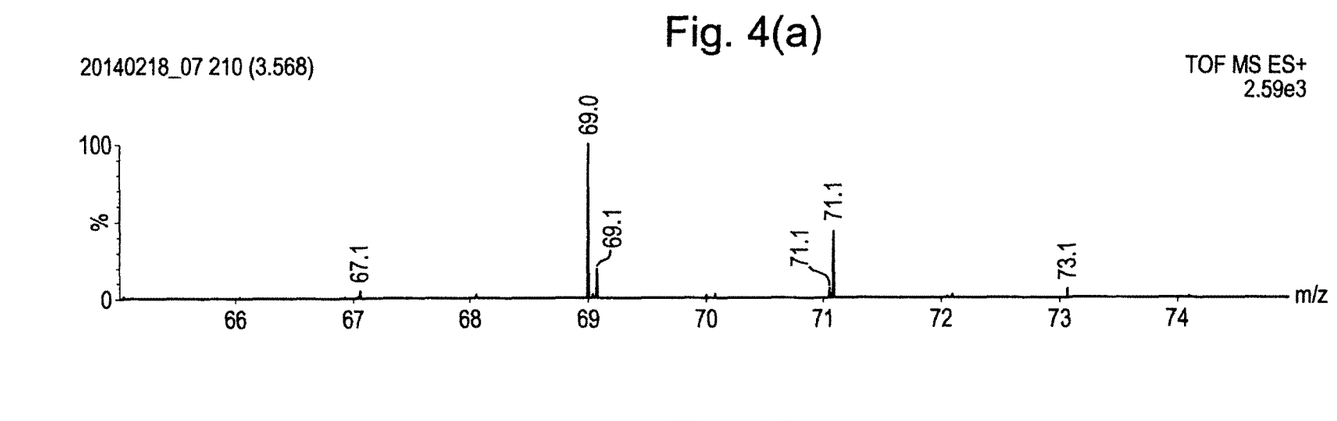
FIGS. 4(a) to 4(d) show mass spectra in a third range of mass to charge ratios that were obtained by analysing Heptacosa using the spectrometer of FIG. 1 under different sampling conditions.
Figure 4B:
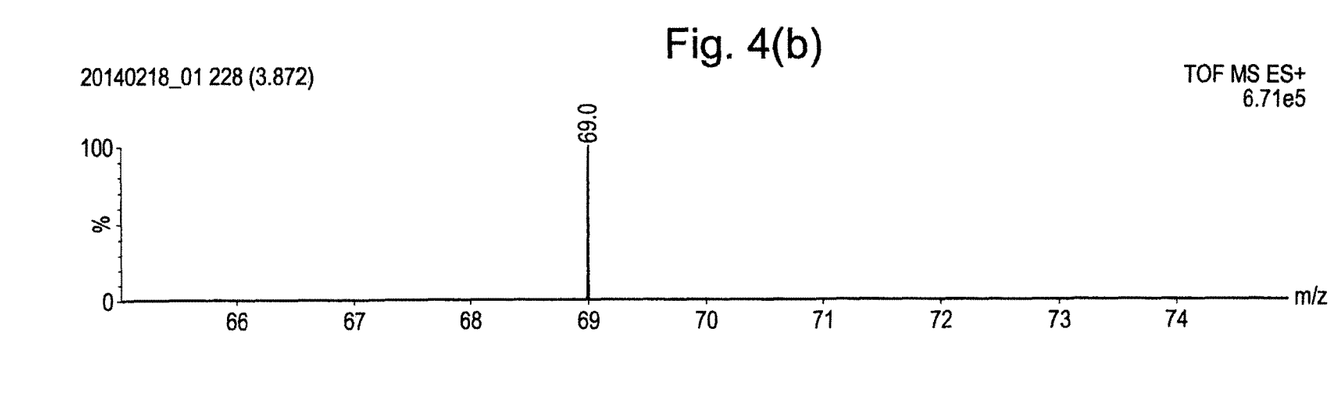
Figure 4C:
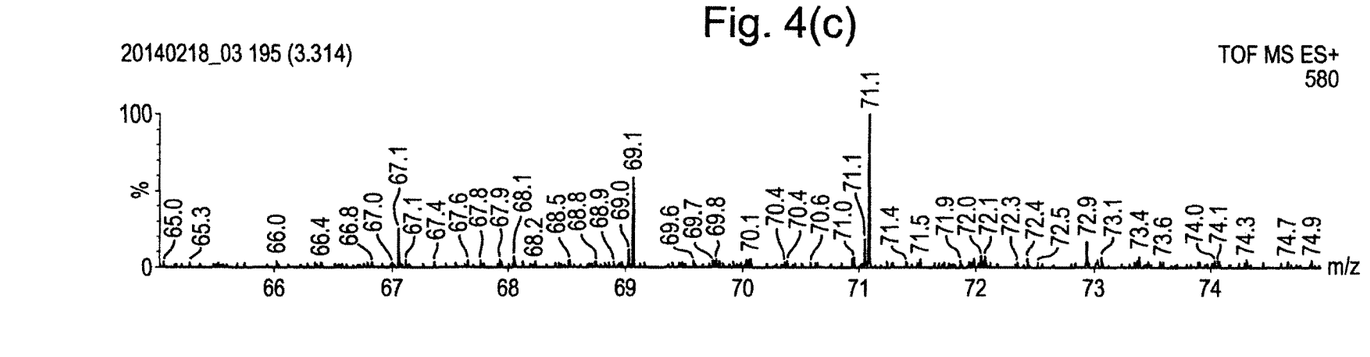
Figure 4D:
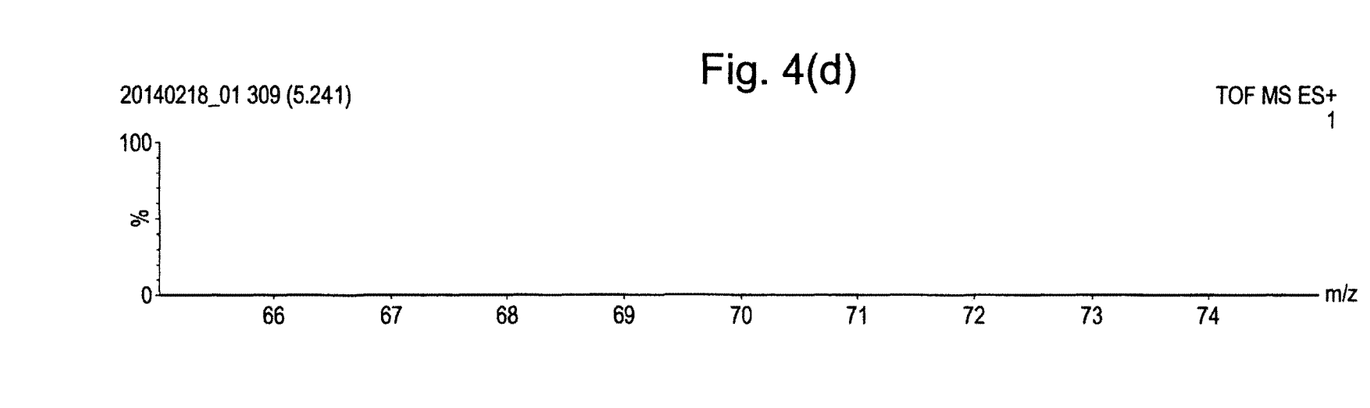

FIGS. 4(a) to 4(d) show spectra obtained under the same conditions as those of FIGS. 2(a) to 2(d), respectively, except that FIGS. 4(a) to 4(d) show the spectra for a different range of mass to charge ratios. FIGS. 4(a) and 4(b) show that a peak associated with Heptacosa is observed at a mass to charge ratio of 69.0.

Although the present invention has been described with reference to some embodiments, it will be understood by those skilled in the art that various changes in form and detail may be made without departing from the scope of the invention as set forth in the accompanying claims.

Although techniques have been described above wherein either the ESI source is switched on or a glow discharge is provided, it is also contemplated that the present invention may provide both forms of ionisation mechanism. In such a method, non-polar analyte molecules in the carrier gas would be ionised via the glow discharge, whilst the ESI source would assist in ionising polar analyte compounds.

It is also contemplated that the analyte could be carried in the solvent emitted from the ESI source, rather than from capillary 2. A glow discharge may then be provided in the vacuum housing for assisting in ionising non-polar compounds.

It will be appreciated that analyte carrier gases and ESI solvents other than those described above may be used, depending upon the sample being analysed.

The carrier gas may be delivered by positive pressure regulated with an MFC.

The analyte sample may be drawn into the instrument using the vacuum within the vacuum housing, i.e. within the ionisation volume.

The analyte sample may be contained within a storage vessel through which the carrier gas is drawn.

The analyte may be sampled directly from the ambient environment via a capillary.

The analyte may be sampled and delivered through the capillary with the assistance of pump (e.g. a Venturi pump).

The analyte sample and/or associated inlet tubing may be heated, e.g. to assist it entering the gas phase efficiently.

The analyte may be introduced into the vacuum housing by direct liquid infusion into the storage vessel.

The analyte solution may be subjected to high performance liquid chromatography (HPLC), gas chromatography (GC) or other chromatography column input before being ionised.

Other means of providing analyte vapour in the reduced pressure region are contemplated, such as direct laser desorption or ablation or thermal desorption of the analyte within the reduced pressure region. This may be performed by directing a laser at a sample plate within the reduced pressure region that contains multiple liquid or crystalline samples.

Means other than an ESI source are contemplated for providing the charged droplets or ions for the ionisation, including sonic spray, atmospheric pressure chemical ionisation (APCI), glow discharge, corona discharge, laserspray, atmospheric pressure matrix assisted laser desorption ionisation (AP-MALDI), atmospheric pressure solids analysis probe (ASAP), or atmospheric pressure photo-ionisation (APPI), etc.

The method may comprise means for volatilising the analyte and introducing it into the sample gas, for example, including ultrasonic or impact induced volatilisation, thermal or laser induced volatilisation, or solvent assisted evaporation.

The ionised analyte may be subjected to electron transfer dissociation (ETD).

The invention claimed is:

1. A method of mass spectrometry or ion mobility spectrometry comprising:
   providing gas phase analyte in a vacuum housing;
   electrospraying a reagent solution outside of the vacuum housing in a region substantially at atmospheric pressure so as to form charged droplets of reagent solution and/or reagent ions;
   conveying the electrosprayed charged droplets and/or reagent ions into the vacuum housing and reacting them with the analyte in a region of the vacuum housing that is below atmospheric pressure so as to form analyte ions; and
   analysing the analyte ions with a mass analyser and/or ion mobility analyser.

2. The method of claim 1, wherein the electrosprayed charged droplets and/or reagent ions pass into the vacuum housing through an atmospheric pressure sampling orifice.

3. The method of claim 1, wherein the electrosprayed charged droplets enter the vacuum housing and then desolvate to form gas phase reagent ions that subsequently react with the analyte to form said analyte ions.

4. The method of claim 1, wherein the analyte is conveyed into the vacuum housing entrained in a gas.

5. The method of claim 1, comprising urging the analyte ions into the mass analyser and/or ion mobility analyser using a pressure gradient and/or electric field.

6. The method of claim 1, comprising drawing the analyte into the vacuum housing using a pressure difference maintained between the inside and outside of the vacuum housing.

7. The method of claim 1, further comprising ionising the analyte within the vacuum housing by a further ionisation means in addition to reacting the analyte with said electrosprayed charged droplets and/or reagent ions.

8. The method of claim 1, comprising heating a sample comprising said analyte so as to provide the gas phase analyte.

9. The method of claim 1, wherein the analyte is provided in the gaseous phase by one of the means selected from the group consisting of: entraining the analyte in a carrier gas that is directed into the vacuum housing; or direct laser desorption, ablation or thermal desorption of the analyte within the reduced pressure region.

10. A mass spectrometer or ion mobility spectrometer comprising:
   a vacuum housing;
   an analyte source for providing gas phase analyte in or to the vacuum housing;
   an electrosprayer arranged outside of the vacuum housing;
   a reagent source for supplying a reagent solution to the electrosprayer for electrospraying charged droplets of reagent solution and/or reagent ions from the electrosprayer into a region substantially at atmospheric pressure;
   conveying apparatus for conveying the electrosprayed charged droplets and/or reagent ions into the vacuum housing for reacting them with the analyte in a region of the vacuum housing that is below atmospheric pressure so as to form analyte ions; and
   a mass analyser and/or ion mobility analyser for analysing the analyte ions.

11. The method of claim 1, wherein a stream of electrosprayed charged droplets and/or reagent ions pass through the vacuum housing in one direction and the gas phase analyte is injected into the vacuum housing substantially orthogonally to the stream of charged droplets and/or reagent ions.

12. A method of mass spectrometry or ion mobility spectrometry comprising:
   passing an analyte through a liquid or gas chromatography device and a heated capillary so as to provide a gas phase analyte;
   drawing the gas phase analyte into a vacuum housing, entrained in a gas, by a pressure difference maintained between the inside and outside of the vacuum housing;
   electrospraying a reagent solution outside of the vacuum housing in a region substantially at atmospheric pressure so as to form charged droplets of reagent solution;
   conveying the electrosprayed charged droplets into the vacuum housing through an atmospheric pressure sampling orifice, wherein the electrosprayed charged droplets desolvate after entering the vacuum housing to form gas phase reagent ions;
   reacting the reagent ions with the analyte in a region of the vacuum housing that is below atmospheric pressure so as to form analyte ions;
   urging the analyte ions into a mass analyser and/or ion mobility analyser using a pressure gradient and/or electric field; and
   analysing the analyte ions with the mass analyser and/or ion mobility analyser.

13. The method of claim 12, wherein a stream of the electrosprayed charged droplets pass through the vacuum housing in one direction and the gas phase analyte is injected into the vacuum housing substantially orthogonally to the stream of charged droplets.

* * * * *